US00PP37378P2

(12) United States Plant Patent
Jackson et al.

(10) Patent No.: US PP37,378 P2
(45) Date of Patent: Apr. 21, 2026

(54) ***CERCIS* PLANT NAMED 'JN104'**

(50) Latin Name: *Cercis canadensis*
Varietal Denomination: JN104

(71) Applicants: Ray Jackson, Belvidere, TN (US); Cindy Jackson, Belvidere, TN (US)

(72) Inventors: Ray Jackson, Belvidere, TN (US); Cindy Jackson, Belvidere, TN (US)

(73) Assignee: GREENLEAF NURSERY CO., Park Hill, OK (US)

( * ) Notice: Subject to any disclaimer, the term of this patent is extended or adjusted under 35 U.S.C. 154(b) by 4 days.

(21) Appl. No.: 18/799,948

(22) Filed: Aug. 9, 2024

(51) Int. Cl.
*A01H 5/00* (2018.01)
*A01H 6/54* (2018.01)

(52) U.S. Cl.
USPC ..... Plt./216

(58) Field of Classification Search
USPC ..... Plt./216
CPC ... A01H 5/04; A01H 5/12; A01H 5/02; A01H 5/00; A01H 6/54
See application file for complete search history.

(56) References Cited

PUBLICATIONS

Sooner Plant Farm, Green Machine Weeping Redbud, retrieved on Apr. 15, 2025 at https://www.soonerplantfarm.com/plant/redbud-green-machine-weeping, 6 pp. (Year: 2025).*

* cited by examiner

*Primary Examiner* — June Hwu
(74) *Attorney, Agent, or Firm* — Penny J. Aguirre

(57) ABSTRACT

A new cultivar of *Cercis canadensis* tree named 'JN104' that is characterized by its deep green foliage, its foliage that is resistant to summer heat in Southern climates, its vigorous, weeping, and consistent growth habit, and its uniform branching.

2 Drawing Sheets

Figure 1:
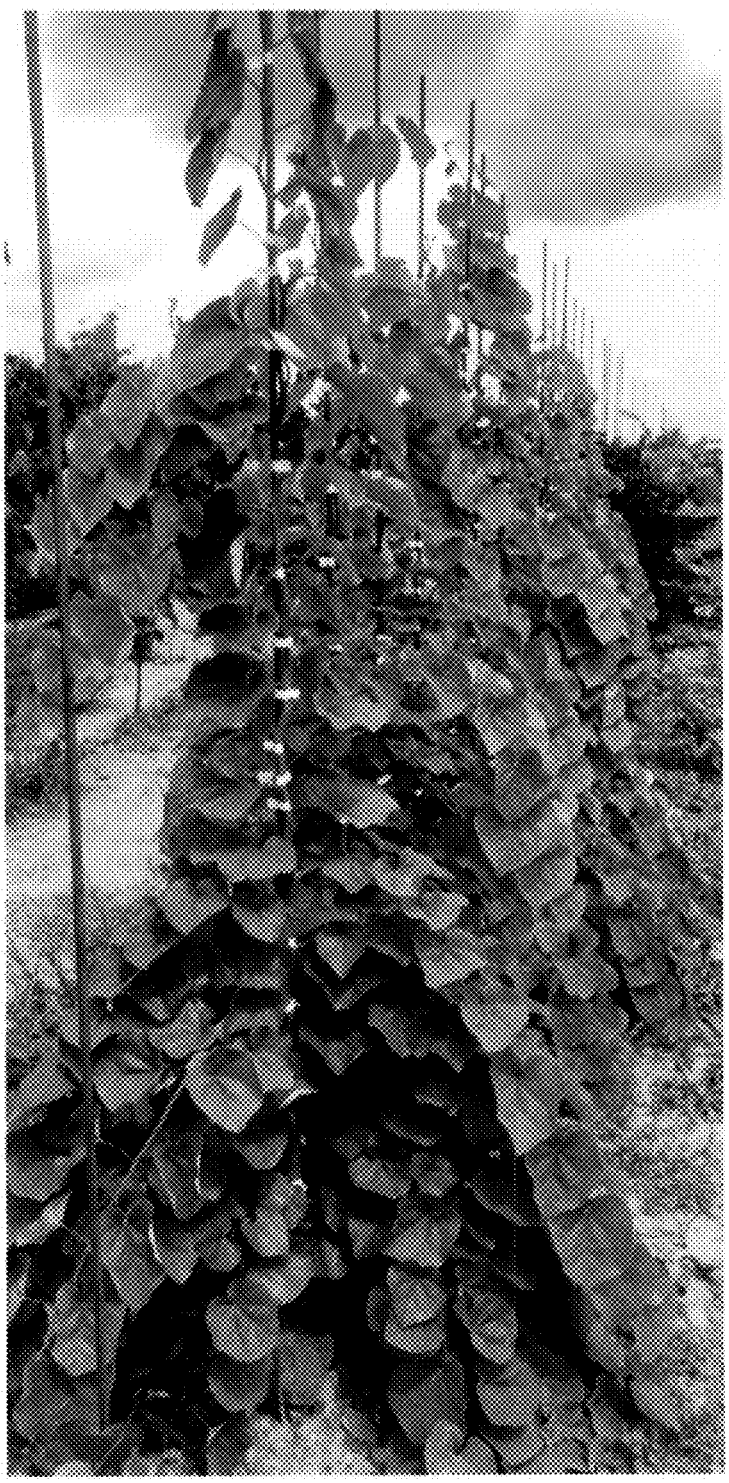

Botanical classification: *Cercis canadensis.*
Variety denomination: 'JN104'.

CROSS-REFERENCE TO RELATED APPLICATIONS

This application is co-pending with U.S. Plant Patent Applications filed for plants derived from the same breeding program that are entitled *Cercis* Tree Named 'JN100' (U.S. Plant patent application Ser. No. 18/799,941), *Cercis* Tree Named 'JN106' (U.S. Plant patent application Ser. No. 18/799,953), and *Cercis* Tree Named 'JN31' (U.S. Plant patent application Ser. No. 18/799,927).

The present invention relates to a new and distinct cultivar of *Cercis canadensis* and will be referred to hereafter by its cultivar name, 'JN104'. 'JN104' is an Eastern redbud tree grown for use as a landscape plant.

The new *Cercis* was selected the new cultivar by the Inventors in summer of 2019 in a cultivated field in Belvidere, Tennessee. The field had been planted with seeds collected in 2016 and pooled from *Cercis canadensis* cultivars 'JN2' (U.S. Plant Pat. No. 21,451) and 'Ruby Falls' (U.S. Plant Pat. No. 22,097). As the two cultivars were the only cultivars growing in the area of seed collection, they are presumed to be the parent plants, however it is unknown which plants are the male or female parent.

Asexual propagation of the new cultivar was first accomplished by budding onto seedling understock of *Cercis canadensis* by one of the Inventors in August of 2019 in Belvidere, Tennessee. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'JN104' as a unique cultivar of *Cercis.*

1. 'JN104' exhibits deep green foliage.
2. 'JN104' exhibits foliage that is resistant to summer heat in Southern climates.
3. 'JN104' exhibits a vigorous, weeping, and consistent growth habit.
4. 'JN104' exhibits uniform branching.

The probable parent plant, 'JN2', differs from 'JN104' in having yellow and tangerine emerging foliage. The probable parent plant, 'Ruby Falls', differs 'JN104' in having purple emerging foliage. 'JN104' can be compared to the *Cercis canadensis* cultivar 'Covey' (U.S. Plant Pat. No. 10,328). 'Covey' is similar to 'JN104' in having a weeping plant habit and green foliage. 'Covey' differs from 'JN104' in having a less vigorous growth habit, a larger leaf size, and less consistent branching habit.

'JN104' can also be compared to the co-pending cultivars of *Cercis canadensis* 'JN100', 'JN106' and 'JN31'. 'JN100' differs from 'JN104' in having foliage that emerges bright red and orange that changes to green in color and a more upright plant habit. 'JN106' differs from 'JN104' in having foliage that emerges burgundy purple that changes to dark green in color. 'JN31' differs from 'JN104' in having foliage that emerges bright yellow in color and changes to chartreuse green as the foliage matures.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Website listings include but may not be limited to listings by Plumline Nursery, Cascadian Nurseries, SiteOne landscape Supply, Bast Brothers Garden Center (Pinterest), Swift Creek Nursery, Creekside Nursery, The Green Machine Nursery & Landscaping, Gardenith, Bob Wells Nursery, Smith's Gardentown, and Sooner Plant Farm.

BRIEF DESCRIPTION OF THE DRA WINGS

The accompanying color photographs illustrate the overall appearance and distinct characteristics of the new *Cercis*. The photographs were taken of 3-year-old plants of the new cultivar as grown in a 5-gallon container in Belvidere, Tennessee.

The photograph in FIG. 1 provides a view of a row of plant of 'JN104' tied to stakes.

Figure 2:
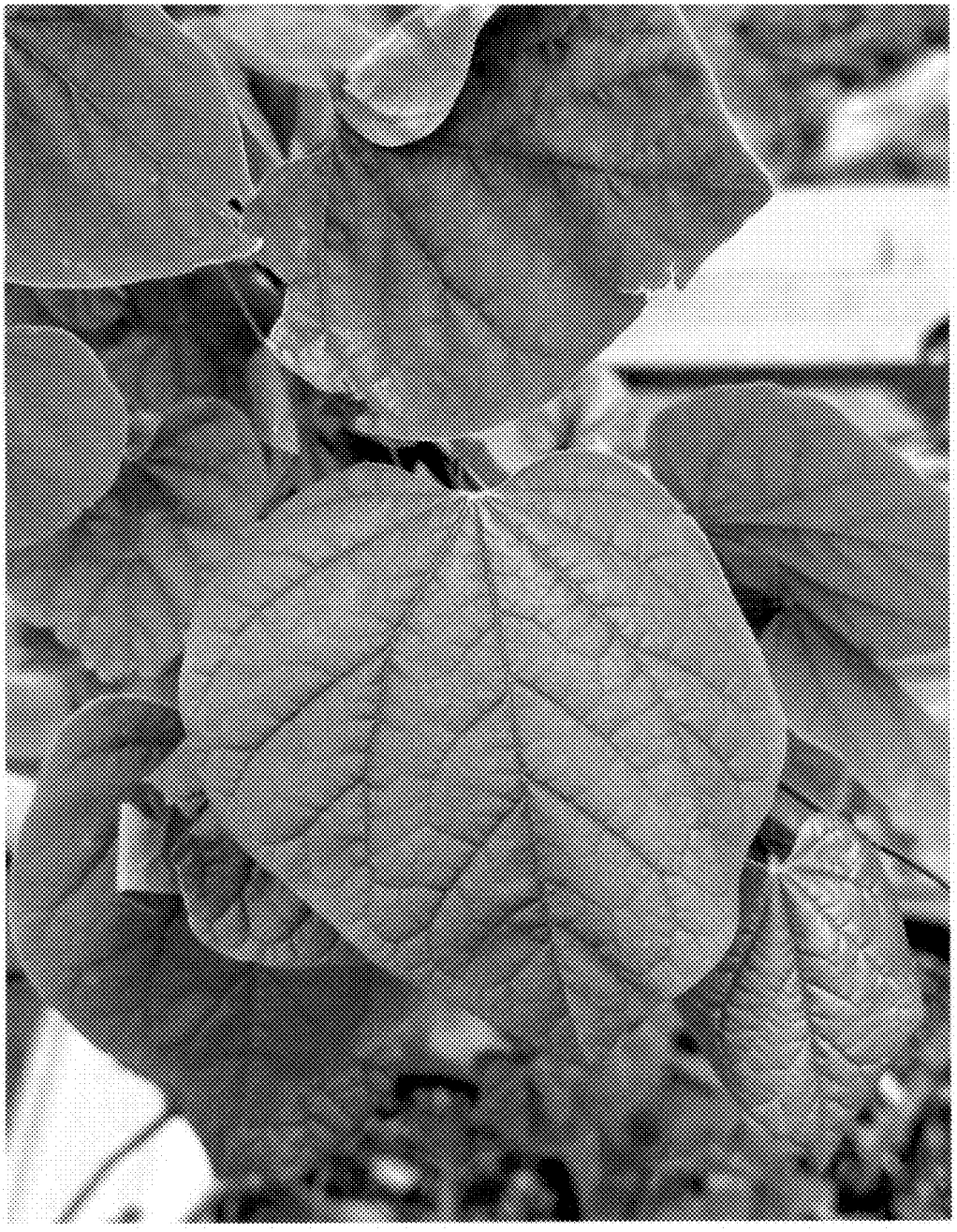

The photograph in FIG. 2 provides a close-up view of the foliage of 'JN104'.

The colors in the photographs are as close as possible with the digital photography techniques available, the color values cited in the detailed botanical description accurately describe the colors of the new *Cercis*.

DETAILED BOTANICAL DESCRIPTION

The following is a detailed description of a 3-year-old plants of the new cultivar as grown in a 5-gallon container in Belvidere, Tennessee. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—3 to 4 weeks in early spring in Belvidere, Tennessee.

*Plant type.*—Deciduous tree.

*Plant habit.*—Weeping and densely branched.

*Height and spread.*—Average of 1.2 m in height, 51 cm in width as a container plant staked, as a mature tree reaches between 1.8 m and 2.4 m in height and between 91 cm to 1.8 m in spread in the landscape.

*Cold hardiness.*—At least to U.S.D.A. Zone 5.

*Diseases and pests.*—No susceptibility or resistance to diseases or pests has been observed.

*Root description.*—Fibrous, 200A in color.

*Propagation.*—Budding.

*Propagation timing.*—Budding in July-August, growth begins in the spring and takes 7 months to become a salable whip.

*Growth rate.*—Vigorous.

Branch and trunk description:

*Trunk.*—An average of 3 cm in diameter and 23 cm in length (until lateral branching), surface of bark; very densely covered with lenticels that completely cover the bark surface 196A and 197A in color.

*Branch shape.*—Rounded, slightly zig-zag growth habit.

*Branch color.*—New growth, 145A, mature branches; N200B to N200C, flushed with N200A, moderately covered with lenticels 155A in color, an average of 15 per sq. cm, linear to oblong in shape, an average of 1 mm in width and 2 mm in length.

*Branch size.*—An average of 72 cm in length and 3 cm in width, new growth; an average of 7 cm in length, 2 mm in diameter.

*Branch surface.*—Young branches; glabrous, semi-glossy, mature bark; glabrous, matte, lustrous, relatively smooth, and very heavily lenticellate.

*Internode length.*—An average of 3 cm.

*Branching habit.*—Weeping, an average of 12 lateral branches per main branch, 25 branches per lateral branch.

Foliage description:

*Leaf shape.*—Ovate-reniform.

*Leaf division.*—Simple.

*Leaf base.*—Cordate.

*Leaf apex.*—Acute to slightly acuminate.

*Leaf fragrance.*—None.

*Leaf venation.*—Palmate, color is not distinguishable from leaf color.

*Leaf margins.*—Entire.

*Leaf arrangement.*—Alternate.

*Leaf aspect.*—Held reflexed slightly downward from petiole (hanging) to horizontal.

*Leaf attachment.*—Petiolate.

*Leaf number.*—An average of 60 leaves per lateral branch.

*Leaf surface.*—Young; both surfaces very glossy, glabrous, slightly translucent, mature; upper surface is glabrous, slightly velvety, and matte, lower surface is glabrous and slightly sheen.

*Leaf size.*—An average of 9 cm in length and 8.5 cm in width.

*Leaf color.*—Emerging and young; both surfaces 144A and N144A, mature; upper surface 144A and 143A, lower surface 146B, fall; a blend of 162A and 20A on both surfaces.

*Petiole.*—An average of 3.8 cm in length and 2 mm in width, glabrous and glossy surface, flexible and moderately strong, 146B in color.

Inflorescence description:

*Inflorescence type.*—Cauliflorous clusters of papilionaceous (pea-like) flowers.

*Inflorescence size.*—Up to 4 cm in width and 3.5 cm in depth.

*Lastingness of inflorescence.*—2 to 3 weeks.

*Flower size.*—An average of 1.2 cm in length and width.

*Flower fragrance.*—Faint.

*Flower number.*—An average of 8 flowers per cluster.

*Bracts.*—Average of 7, surrounding base of inflorescence, whorled, imbricate, ovate in shape, acute apex, an average of 0.75 mm in length and width, color; 200A, glabrous and matte surfaces.

*Peduncles.*—An average of 1.8 cm in length and 0.5 mm in diameter, color; 187C, slightly glossy surface, moderately strong, held straight from base to slightly curved, held at all directions from branch node in a whorled arrangement.

*Pedicels.*—None, peduncles attached in cluster at branch.

*Flower buds*.—Slightly curved, beak-shaped, 8 mm in length, 3 mm in width, glabrous and matte surfaces, color; 77B.

*Flower type*.—Papilionaceous.

*Calyx*.—Campanulate in shape, 4 mm in length, 3.5 mm in diameter.

*Sepals*.—5, 95% of base fused, 3 mm in length, free part of sepal 1 mm in length and width, bluntly acute apex, entire margins, both surfaces are glabrous and matte, both surfaces 187A in color.

*Corolla features*.—Papilionaceous, bilateral with two upper petals around the stamens and pistil, a center petal, and two lower petals under the center petal, upper petals; elliptic and cup shaped, margins slightly undulate, average of 9 mm in length, 6 mm in width, both surfaces glabrous, slightly glossy, color when opening and fully open; N78A, N78C, base 84D, fading to 91A, center petal; 2 mm in length, 3 mm in width, both surfaces glabrous, slightly glossy, broad in shape and curled downward, rounded apex, cuneate base, entire margins, slightly undulate, color when opening and fully open; N78A, N78C, base 84D, fading to 91A, lower petals; elliptical to in shape, curled downward, margins moderately undulate, average of 8.5 mm in length, 3 mm in width, both surfaces glabrous, slightly glossy and slightly transparent at the base, color when opening and fully open; N78A, N78C, base 84D, fading to 91A.

Reproductive organs:

*Gynoecium*.—Pistil; 1, stigma; very small, round, 0.3 mm in diameter, 19C in color, slightly transparent, style; an average of 8 mm in length, 1 mm in width, 61A in color, ovary; round, in bottom of calyx, N92A in color.

*Androecium*.—Stamens; 10, anthers; oval shaped, an average of 0.8 mm in diameter, 200A in color, filament; an average of 5 mm in length and 0.8 mm in width, color; N80B, glossy and transparent surface, pollen is abundant in quantity, 19C in color.

*Seed and fruit*.—None observed to date.

It is claimed:

1. A new and distinct cultivar of *Cercis canadensis* tree named 'JN104' as herein illustrated and described.

* * * * *